(12) United States Patent
Laurin et al.

(10) Patent No.: US 10,995,204 B2
(45) Date of Patent: May 4, 2021

(54) GLASS-FILLED POLYPROPYLENE COMPOSITIONS

(71) Applicant: SABIC Global Technologies B.V., Bergen op Zoom (NL)

(72) Inventors: Michael M. Laurin, San Pedro, CA (US); Craig Lawrence Milne, Pittsfield, MA (US); Rein Mollerus Faber, Bergen op Zoom (NL); Manish Nandi, Malvern, PA (US); Christianus Johannes Jacobus Maas, Rilland (NL); Hochul Jung, Perry, OH (US); Mohammad Moniruzzaman, Exton, PA (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 118 days.

(21) Appl. No.: 16/318,048

(22) PCT Filed: Jul. 18, 2017

(86) PCT No.: PCT/US2017/042554
§ 371 (c)(1),
(2) Date: Jan. 15, 2019

(87) PCT Pub. No.: WO2018/017551
PCT Pub. Date: Jan. 25, 2018

(65) Prior Publication Data
US 2020/0247983 A1 Aug. 6, 2020

Related U.S. Application Data

(60) Provisional application No. 62/364,667, filed on Jul. 20, 2016.

(51) Int. Cl.
| | | |
|---|---|---|
| *C08L 23/12* | (2006.01) | |
| *B29C 70/12* | (2006.01) | |
| *C08J 5/04* | (2006.01) | |
| *C08K 7/14* | (2006.01) | |

(52) U.S. Cl.
CPC .............. *C08L 23/12* (2013.01); *B29C 70/12* (2013.01); *C08J 5/043* (2013.01); *C08J 2323/12* (2013.01); *C08K 7/14* (2013.01); *C08K 2201/004* (2013.01)

(58) Field of Classification Search
CPC . C08K 7/14; C08J 5/043; C08L 23/12; B29C 70/12
See application file for complete search history.

(56) References Cited

U.S. PATENT DOCUMENTS

| | | | |
|---|---|---|---|
| 5,883,159 | A | 3/1999 | Koizumi et al. |
| 6,216,811 | B1 | 4/2001 | Herc |
| 6,299,258 | B1 | 10/2001 | Wright et al. |
| 6,528,302 | B2 | 3/2003 | Turner et al. |
| 6,685,864 | B2 | 2/2004 | Bingle et al. |
| 6,689,446 | B2 | 2/2004 | Barnes et al. |
| 7,240,876 | B2 | 7/2007 | Doubleday et al. |
| 8,413,837 | B2 | 4/2013 | Bollengier |
| 9,131,871 | B2 | 9/2015 | Boersma et al. |
| 2010/0102055 | A1 | 4/2010 | Becklin |
| 2015/0200470 | A1 | 7/2015 | Bertness |

FOREIGN PATENT DOCUMENTS

| | | |
|---|---|---|
| CN | 101875740 A | 11/2010 |
| CN | 101987603 A | 3/2011 |
| CN | 102127259 A | 7/2011 |
| CN | 202209971 U | 5/2012 |
| CN | 102516667 A | 6/2012 |
| CN | 102702614 A | 10/2012 |
| CN | 202595300 U | 12/2012 |
| CN | 103160017 A | 6/2013 |
| CN | 103183168 A | 7/2013 |
| CN | 103589103 A | 2/2014 |
| CN | 103788491 A | 5/2014 |
| JP | 2011-173948 A | 9/2011 |
| WO | WO 2013/149915 A1 | 10/2013 |
| WO | WO 2015/028955 A1 | 3/2015 |
| WO | WO 2015/039237 A1 | 3/2015 |
| WO | WO 2015/053808 A1 | 4/2015 |

OTHER PUBLICATIONS

International Patent Application No. PCT/US2017/042554; Int'l Search Report and the Written Opinion; dated Dec. 8, 2017; 11 pages.
International Patent Application No. PCT/US2017/042554; Int'l Preliminary Report on Patentability; dated Jan. 31, 2019; 7 pages.

*Primary Examiner* — Edward J Cain
(74) *Attorney, Agent, or Firm* — Cantor Colburn LLP

(57) ABSTRACT

A fiber-reinforced thermoplastic composition includes a polypropylene polymer component including a low flow grade polypropylene and a high flow grade polypropylene, and a fiber reinforcement component. The fiber-reinforced thermoplastic composition is capable of being vacuum formed. In another aspect a thermoplastic composition includes a homopolymer component including polypropylene, a co-polymer component, an impact modifier, and one or more of a flame retardant component and a fiber reinforcement component. The thermoplastic composition is capable of being vacuum formed. The fiber-reinforced thermoplastic composition may be formed into an article such as an enclosure for an electrical component, and it may be chemically resistant to a medical grade cleaner.

20 Claims, No Drawings

GLASS-FILLED POLYPROPYLENE COMPOSITIONS

CROSS-REFERENCE TO RELATED APPLICATION

This application is the National Stage of International Application No. PCT/US2017/042554, filed Jul. 18, 2017, which claims the benefit of U.S. Provisional Application No. 62/364,667 filed Jul. 20, 2016, the disclosures of which are incorporated herein by this reference in their entireties.

TECHNICAL FIELD

The present disclosure relates to glass-filled polypropylene compositions, articles, and methods of making the same.

TECHNICAL BACKGROUND

Glass fiber is typically added to semi-crystalline materials, such as, for example, polypropylene materials, to maintain or improve dimensional stability under extreme temperatures. Unfortunately, the addition of glass fiber also results in diminished elastic properties. Similarly, long fiber reinforcements in thermoplastic resin can improve impact properties of the product. Presence of the long fibers in the composite, however, can also result in an unwanted brittleness of the composite, which can limit its applicability due to performance concerns.

Accordingly, there remains a need for thermoplastic compositions and methods of forming article from the same that can provide improved impact strength properties and other improved properties including the ability to be sterilized for medical applications. These needs and other needs are satisfied by the compositions, articles, and methods of the present disclosure.

SUMMARY

Aspects of the disclosure relate to fiber-reinforced thermoplastic polymer compositions capable of being formed into articles such as surgical trays. Accordingly, in a first aspect, the present disclosure includes a fiber-reinforced thermoplastic composition, including a polypropylene polymer component and a fiber-reinforcement component. The thermoplastic composition is capable of being vacuum formed into a surgical tray.

Aspects of the disclosure further relate to articles formed from the fiber-reinforced thermoplastic composition under a heater profile optimized or configured for surface area heating at a perimeter of a plaque such that the center heat minimizes plaque thinning and radius stretch through side walls, thereby retaining maximum wall thickness. Such a heater profile may make use of pressurized halogen heaters.

DETAILED DESCRIPTION

Fiber-reinforced thermoset plastics have traditionally been used in performance demanding applications, including but not limited to aerospace applications. Recently, however, the medical industry has started looking at fiber-filled thermoplastic composites due to their improved ductility and impact resistance, thermoformability, shorter production cycle, and recyclability. These improvements increase the likelihood of articles meeting government regulations. Additionally, these improvements are cost-effective, a feature that may be important to medical device manufacturers. As a particular example, articles may include enclosures for electronic devices or electrical components. The enclosures may include the compositions described herein. Moreover, the enclosures may be chemically resistant to certain solvents and cleaners, for example surgical cleaners used in medical environments.

To obtain optimum performance of thermoplastic-based composite, it may be desirable to use polypropylene (PP) reinforced with glass fibers (GF). Such GF-PP composite typically is readily available, thus making it very economical, and in application, demonstrates improved impact resistance in automobile bumpers and lateral door supports, for example.

The performance of GF-PP can be determined by the properties of the PP, the glass fibers, and the interface between them. PP is a semi-crystalline thermoplastic in which the crystalline phase plays a critical role in defining the macroscopic properties of the entire composite. Crystallization is a thermodynamic process that depends mainly on the cooling rate during the last stage of the manufacturing cycle. Rapid cooling is certainly beneficial to composites manufacturers because the total processing time can be reduced. However, it is important to understand how the heating and cooling affects the mechanical properties of the resulting PP and its composites.

It has been shown that the cooling rate affects both the crystallinity (ratio of the crystalline phase to the amorphous phase) and the morphology (the size of crystals, which are usually called spherulites). Generally, increasing the cooling rate reduces both the crystallinity and the size of spherulites in neat homopolymer PP and its composites. These reductions impact the mechanical performance of GF-PP: increasing the cooling rate improves the flexural strength, in-plane shear strength, strain at failure, and tensile/opening (mode I) and in-plane shear (mode II) fracture toughness.

It has further been shown that the cooling rate also affects the fiber-matrix interface of classical GF-PP. Scanning electron microscope (SEM) observation of failed GF-PP laminates reveals that most of the damage in rapidly cooled samples occurs in the bulk PP matrix, while the damage in slowly cooled samples is mostly characterized by fiber-matrix debonding. These observations substantiate the results of single fiber pull-out tests, which show that the fiber-matrix interfacial shear strength (IFSS) of a glass fiber in quenched PP is higher than that of a glass fiber in isothermally crystallized PP at a dwelling temperature of 140 degrees Celsius (° C.).

Moreover, the mechanisms used in applying heat to a plaque for forming various articles may be optimized. For example, pressurized halogen heaters may be used to apply heat to a plaque formed from compositions described herein. Pressurized halogen heaters may comprise halogen gas that is pressurized and produces intense heat. As another example, the heaters may have maximum operating temperature between 1500-3000° C. and maximum intensity between 0.80 micrometers (microns, μm) and 2 μm. As a further example, the heaters may have maximum operating temperature at about 2700° C. and maximum intensity at about 0.90 μm. Further, the heater profile may be optimized or configured for surface area heating at a perimeter of plaque such that the center heat minimizes plaque thinning and radius stretch through side walls, thereby retaining maximum wall thickness.

As briefly summarized above, aspects of the present disclosure provide fiber-reinforced thermoplastic polymer compositions that exhibit one or more improved performance properties relative to conventional reinforced thermoplastic compositions. For example, the disclosed fiber-reinforced thermoplastic polymer compositions can exhibit one or more of improved impact properties, improved ductile failure mode, and can exhibit a softer touch or feel along with a relatively low surface gloss. To that end, as one of ordinary skill in the art will appreciate, conventional reinforced thermoplastic materials typically contain a thermoplastic material that has been blended with glass reinforcing fibers to impart rigidity and improve impact strength as evidenced, for example, by a general increase in tensile strength and modulus. However, the addition of reinforcing glass fibers also typically reduces the elastic properties of the thermoplastic material as evidence, for example, by a reduced ductility or tensile elongation or strain.

As noted above, the disclosed compositions comprise a thermoplastic polymer component. The thermoplastic polymer component comprises at least one thermoplastic polymer. in one aspect, the thermoplastic polymer component can comprise a single thermoplastic polymeric material or, alternatively, in another aspect can comprise a blend of two or more different thermoplastic polymer materials. The thermoplastic polymer component can comprise any thermoplastic polymer or mixture of polymers suitable for use in the composition or in an intended application. According to some aspects, the thermoplastic polymer component comprises a polypropylene polymer component. For example, in some aspects the polypropylene component can comprise a polypropylene homopolymer. According to an exemplary non-limiting aspect, a commercially available polypropylene homopolymer suitable for use in the compositions and methods disclosed and described herein is the Innovene™ H20H grade polypropylene available from Ineos Technologies. The Innovener™ H20H grade polypropylene has a melt flow index (MFI) of about 20 grams per 10 minutes (g/10 min) when measured at a temperature of 230° C. and under a 2.16 kilogram (kg) load. In a still further exemplary and non-limiting aspect, one or more of a low flow and high flow grade thermoplastic polymer may be used. Generally, a low flow grade thermoplastic polymer may he described as one having a MFI of less than 20 g/10 min when measured at a temperature of 230° C. and under a 2.16 kg load, and a high flow grade thermoplastic polymer may be described as one having a MFI of greater than or equal to 20 g/10 min when measured at a temperature of 230° C. and under a 2.16 kg load. In one aspect, a low flow PP may include Bapolene® 4042 polypropylene resin (Bamburger Polymers, Inc., MFI of about 4 g/10 minutes when measured at a temperature of 230° C. and under a 2.16 kg load) and a high flow PP may include Bapolene® 4082 polypropylene resin (Bamberger Polymers, Inc., MFI of about 35 g/10 minutes when measured at a temperature of 230° C. and under a 2.16 kg load). As an example, a blend of Bapolene® 4042 low flow PP and Bapolene® 4082 high flow PP may be mixed (with or without other components/additives) to result in a polypropylene with a MFR of between 14 and 18 g/10 minutes when measured at a temperature of 210° C. and under a 5 kg load. Loadings of one or more of the low flow and high flow materials may include 30% high flow and 70% low flow relative to the PP blend and 50% low flow with 30% high flow including the remaining 20% of additives and other components resulting in 100% wt of the overall blended composition.

Alternatively, the polypropylene component can comprise a polypropylene co-polymer. The thermoplastic polymer component can be present in the composition in any desired amount. However, in some aspects the thermoplastic polymer component be present in the composition in an amount in the range of from about 10 weight percent (wt. %) to 90 wt. % of the composition, including such exemplary amounts as 15, 20, 25, 30, 35, 40, 45, 50, 55, 60, 65, 70, 75, 80, or 85 wt. %. In still further aspects, the thermoplastic polymer component can be present in an amount within any range derived from any two of the above values, including for example, an amount in the range of from 10 wt. % to 70 wt. %, or an amount in the range of from 20 wt. % to 70 wt. %.

As also noted above, the disclosed compositions further comprise a low melt flow elastomer component. The low melt flow elastomer component can be characterized by having a melt flow index (MFI) value less than 30 g/10 minutes when measured at a temperature of 190° C. and under a 2.16 kg load. In further aspects, the low melt flow elastomer component can exhibit a melt flow index value less than 25 g/10 minutes, less than 20 g/10 minutes, less than 15 g/10 minutes, less than 10 g/10 minutes, or even less than 5 g/10 minutes when measured at a temperature of 190° C. and under a 2.16 kg load. In still further aspects, the low melt flow elastomer component exhibits a melt flow index in any range derived from any two of the above disclosed melt flow index values, including for example, a melt flow index in the range of from 5 to 20 g/10 minutes when measured at a temperature of 190° C. and under a 2.16 kg load. As used herein, melt flow index values can, for example and without limitation, be determined according to the ASTM D1238 testing protocol.

Exemplary low melt flow elastomers suitable for use in the disclosed compositions include the class of ethylene containing elastomers, including for example ethylene-butene copolymer elastomers and ethylene-octene copolymer elastomers. Similar to the thermoplastic polymer component, the low melt flow elastomer component can comprise a single low melt flow elastomer or, alternatively, can comprise a blend of two or more different low melt flow elastomers. Further, although the low melt flow elastomer component can be present in the composition in any desired amount, it can be preferable according to some aspects for the low melt flow elastomer component to be present in the composition in an amount in the range of from greater than 0 wt. % to 30 wt. %, including exemplary amounts of 1 wt. %, 5 wt. %, 10 wt. %, 15 wt. %, 20 wt. %, and 25 wt. %. In still further aspects, the low melt flow elastomer component can be present in the composition in an amount in any range derived from any two of the above disclosed wt. % values, including for example from 5 to 20 wt. % or from 10 to 20 wt. %. An exemplary non-limiting example of a commercially available ethylene-butene elastomer suitable for use in the compositions and methods disclosed herein is the Engage™ 7447 available from Dow Chemicals. Exemplary non-limiting examples of commercially available ethylene-octene elastomers suitable for use in the compositions and methods disclosed herein include Engage™ 8200, Engage™ 8137 and Engage™ 8407, all of which are also available from Dow Chemicals.

The disclosed compositions further comprise a fiber reinforcement component. Preferably, the fiber reinforcement component comprises a plurality of glass fibers. To that end, the glass fibers can be relatively short glass fibers, relatively long glass fibers, or a combination of both short and long glass fibers. As used herein, the term short glass fibers refers to a population of glass fibers having an average fiber length less than or equal to about 5 millimeters (mm). As used herein, the term long glass fibers refers to a population of glass fibers having an average fiber length greater than about 5 mm, including for example, a population of glass fibers having a fiber length in the range of from greater than 5 mm to 15 mm. The fiber reinforcement component can be present in the composition in any desired amount. However, in some aspects, the reinforcement component can be present in the composition in an amount from greater than 0 wt. % to about 70 wt. %, including exemplary amounts of 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, and 65 wt. %. In still further aspects, the fiber reinforcement component can be present in the composition in an amount in any range derived from any two of the above disclosed wt. % values, including for example from 20 to 50 wt. % or from 30 to 50 wt. %. Exemplary long glass fibers include, without limitation, TutRov® 4588 glass fibers commercially available from PPG Industries. Exemplary short or chopped glass fibers suitable for use in disclosed samples, including those prepared by twin screw extrusion compounding as exemplified herein, include without limitation the ThermoFlow™ 738 glass fibers commercially available from Johns Manville.

The disclosed compositions can further comprise one or more optional additive components, including for example, one or more additive selected from the group consisting of a coupling agent, antioxidant, heat stabilizer, flow modifier, and colorant. For example, and without limitation, an exemplary coupling agent suitable for use as an additive component in the disclosed compositions includes the Polybone™ 3150 maleic anhydride grafted polypropylene commercially available from Chemtura or the Fusabond™ P613 maleic anhydride grafted polypropylene commercially available from DuPont. An exemplary flow modifier suitable for use as an additive component in the disclosed compositions can include, without limitation, the CR20P peroxide masterbatch commercially available from Polyvel Inc. Still further, an exemplary stabilizer suitable for use as an additive component in the disclosed compositions can include, without limitation, the Irganox™ B225 commercially available from BASF. In a still further aspect, neat polypropylene can be introduced as an optional additive. For example, neat polypropylene can be introduced in a dry blending step during a molding process to alter levels of glass fiber loading in a composition.

According to aspects of the disclosure, the disclosed fiber-reinforced thermoplastic polymer compositions can exhibit one or more improved performance properties when compared to a conventional or reference composition in the absence of the low melt flow elastomer component. For example, the disclosed compositions can exhibit one or more of improved impact properties, more ductile and less brittle failure modes, a softer touch or feel, and a relatively low surface gloss. Further, it should be understood that these improved properties relative to the comparative reference compositions can be provided in any combination or they can occur individually for a given composition.

In still further aspects, the present disclosure provides methods for the manufacture of the fiber-reinforced thermoplastic compositions described herein. For example, and without limitation, a thermoplastic resin mixture can be provided that comprises a polypropylene polymer component and a reinforcement component.

A provided reinforcing fiber component as described above can then be contacted with the thermoplastic resin mixture to provide a fiber-reinforced thermoplastic composite. As one of ordinary skill in the art will appreciate, this contacting step can vary depending upon the nature of the reinforcing fiber component. For example, according to some aspects the contacting step can be performed by a continuous one step pultrusion process. As one of ordinary skill in the art will appreciate, a pultrusion process is better suited for use in those aspects where the reinforcing fiber material comprises long glass fiber. According to these aspects, glass fiber rovings can be continuously pulled off a spool and through a thermoplastic resin mixture coating or impregnation station where they are coated or impregnated with a melt comprising the thermoplastic resin mixture. The coated or impregnated glass fiber strands can then be cooled and subsequently pelletized. These pellets can then be injection molded into test specimen parts in their existing form for property testing or into molded parts of varying complexity for use in desired end use applications. If one or more optional additives are desired to be incorporated into the fiber-reinforced thermoplastic compositions, they can be introduced either during the pultrusion process or by dry-blending with pelletized reinforced thermoplastic composition following the pultrusion process and before any subsequent molding steps.

In alternative aspects where the fiber reinforcing material comprises short glass fibers, the step of contacting the short glass fibers with the thermoplastic resin mixture can, for example, be performed by compounding the short glass fibers together with the thermoplastic resin mixture. This compounding can be performed using any conventionally known equipment used for the manufacture of fiber-reinforced thermoplastic composite materials, including for example the use of a twin screw extruder. The extruded glass fiber-reinforced composition can then be cooled and subsequently pelletized. These pellets can then be injection molded into test specimen parts in their existing form for property testing or into molded parts of varying complexity for use in desired end use applications. Once again, if one or more optional additives are desired to be incorporated into the fiber-reinforced thermoplastic composition, they can be introduced either during the extrusion process or by dry-blending with pelletized reinforced thermoplastic composition following the extrusion process and before any subsequent molding steps.

The optional additives disclosed herein can be introduced into the compositions either before or during a molding process. For example, one or more optional additives can be introduced into a thermoplastic resin mixture or composition before glass fiber reinforcement components are blended or otherwise introduced into the thermoplastic resin mixture. Alternatively, one or more optional additives can be introduced into a composition after the glass fiber reinforcement component has been blended or otherwise introduced into a composition. In still further aspects, one or more optional additives can be introduced during a dry blending step performed during a molding process.

The fiber-reinforced thermoplastic compositions disclosed and described herein can be used in various end use applications, including in applications where sterilization is required. As an example, a surgical article may be formed comprising a surgical tray including a bottom surface having side walls disposed around a periphery thereof and extending from the bottom surface. The surgical article may be formed using various processes. In certain aspects, vacuum forming may be used. The vacuum forming may include a heater profile optimized or configured to heat a surface area at a perimeter of a plaque such that a plaque thinning at the bottom surface is minimized and radius stretch through the side walls is minimized, thereby retaining maximum wall thickness.

In various aspects, the present disclosure pertains to and includes at least the following aspects.

Aspect 1: A fiber-reinforced thermoplastic composition comprising:
  a) a polypropylene polymer component including a low flow grade polypropylene and a high flow grade polypropylene; and
  b) a fiber reinforcement component,
  wherein the fiber-reinforced thermoplastic composition is capable of being vacuum formed.

Aspect 2: A fiber-reinforced thermoplastic composition consisting of:
  a) a polypropylene polymer component including a low flow grade polypropylene and a high flow grade polypropylene; and
  b) a fiber reinforcement component,
  wherein the fiber-reinforced thermoplastic composition is capable of being vacuum formed.

Aspect 3: A fiber-reinforced thermoplastic composition consisting essentially of:
  a) a polypropylene polymer component including a low flow grade polypropylene and a high flow grade polypropylene; and
  b) a fiber reinforcement component,
  wherein the fiber-reinforced thermoplastic composition is capable of being vacuum formed.

Aspect 4: The fiber-reinforced thermoplastic composition of any one of Aspects 1-3, comprising:
  a) from 10 to 80 weight percent of the polypropylene polymer component; and
  b) from 20 to 90 weight percent of the fiber reinforcement component.

Aspect 5: The fiber-reinforced thermoplastic composition of any one of Aspects 1-4, wherein the fiber-reinforced thermoplastic composition has a melt flow rate (MFR) of between 14 and 18 g/10 minutes when measured at a temperature of 210° C. and under a 5 kg load.

Aspect 6: The fiber-reinforced thermoplastic composition of any one of Aspects 1-5, wherein the vacuum forming comprises a heater profile configured to heat a surface area at a perimeter of a plaque formed from the fiber-reinforced thermoplastic composition.

Aspect 7: The fiber-reinforced thermoplastic composition of Aspect 6, wherein the heater profile is applied via a pressurized halogen heater.

Aspect 8: The fiber-reinforced thermoplastic composition of any one of Aspects 1-7, wherein the polypropylene polymer component comprises a polypropylene homo-polymer.

Aspect 9: The fiber-reinforced thermoplastic composition of any one of Aspects 1-7, wherein the polypropylene polymer component comprises a polypropylene co-polymer.

Aspect 10: The fiber-reinforced thermoplastic composition of any one of Aspects 1-9, wherein the fiber reinforcement component comprises a glass fiber.

Aspect 11: The fiber-reinforced thermoplastic composition of Aspect 10, wherein the fiber reinforcement component comprises a long glass fiber having a length after extrusion or molding of from about 2 mm to about 15 mm.

Aspect 12: The fiber-reinforced thermoplastic composition of Aspect 10, wherein the fiber reinforcement component comprises short glass fibers having a length after extrusion or molding of from about 0.1 mm to about 0.2 mm.

Aspect 13: The fiber-reinforced thermoplastic composition of Aspects 1-12, further comprising one or more additive selected from the group consisting of a coupling agent, heat stabilizer, flow modifier, and colorant.

Aspect 14: The fiber-reinforced thermoplastic composition of any one of Aspects 1-13, wherein the polypropylene polymer component comprises 30% high flow grade polypropylene and 70% low flow grade polypropylene relative to the polypropylene polymer component.

Aspect 15: An article formed from the fiber-reinforced thermoplastic composition of any one of Aspects 1-14.

Aspect 16: The article of Aspect 15, wherein the article comprises an enclosure for an electrical component.

Aspect 17: The article of Aspect 15, wherein the article is chemically resistant to a medical grade cleaner.

Aspect 18: A thermoplastic composition comprising:
  a) a homopolymer component comprising polypropylene;
  b) a co-polymer component;
  c) an impact modifier; and
  d) one or more of a flame retardant component and a fiber reinforcement component,
  wherein the thermoplastic composition is capable of being vacuum formed.

Aspect 19: The thermoplastic composition of Aspect 18, further comprising one or more additives selected from the group consisting of a coupling agent, heat stabilizer, flow modifier, and colorant.

Aspect 20: A thermoplastic composition consisting of:
  a) a homopolymer component comprising polypropylene;
  b) a co-polymer component;
  c) an impact modifier; and
  d) one or more of a flame retardant component and a fiber reinforcement component,
  wherein the thermoplastic composition is capable of being vacuum formed.

Aspect 21: A thermoplastic composition consisting essentially of:
  a) a homopolymer component comprising polypropylene;
  b) a co-polymer component;
  c) an impact modifier; and
  d) one or more of a flame retardant component and a fiber reinforcement component,
  wherein the thermoplastic composition is capable of being vacuum formed.

Aspect 22: An article formed from the thermoplastic composition of any one of Aspects 18-21.

Aspect 23: The article of Aspect 22, wherein the article comprises an enclosure for an electrical component.

Aspect 24: The article of Aspect 22, wherein the article is chemically resistant to a medical grade cleaner.

While typical aspects have been set forth for the purpose of illustration, the foregoing descriptions should not be deemed to be a limitation on the scope of the disclosure. Accordingly, various modifications, adaptations, and alternatives can occur to one skilled in the art without departing from the spirit and scope of the present disclosure.

The present disclosure can be understood more readily by reference to the following detailed description, examples, drawings, and claims, and their previous and following description. However, before the present compositions, articles, devices, systems, and/or methods are disclosed and described, it is to be understood that this disclosure is not limited to the specific aspects of compositions, articles, devices, systems, and/or methods disclosed unless otherwise specified, as such can, of course, vary. It is also to be understood that the terminology used herein is for the purpose of describing particular aspects of the disclosure only and is not intended to be limiting.

The following description of the disclosure is also provided as an enabling teaching of the disclosure in its best, currently known aspect. To this end, those of ordinary skill in the relevant art will recognize and appreciate that changes and modifications can be made to the various aspects of the disclosure described herein, while still obtaining the beneficial results of the present disclosure. It will also be apparent that some of the desired benefits of the present disclosure can be obtained by selecting some of the features of the present disclosure without utilizing other features. Accordingly, those of ordinary skill in the relevant art will recognize that many modifications and adaptations to the present disclosure are possible and can even be desirable in certain circumstances and are thus also a part of the present disclosure. Thus, the following description is provided as illustrative of the principles of the present disclosure and not in limitation thereof.

Various combinations of elements of this disclosure are encompassed by this disclosure, e.g. combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

Any publications mentioned herein are incorporated herein by reference to disclose and describe the methods and/or materials in connection with which the publications are cited.

It is also to be understood that the terminology used herein is for the purpose of describing particular aspects only and is not intended to be limiting. As used in the specification and in the claims, the term "comprising" may include the aspects or aspects "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a glass fiber" includes mixtures of two or more such glass fibers.

Ranges can be expressed herein as from one value (first value) to another value (second value). When such a range is expressed, the range includes in some aspects one or both of the first value and the second value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. it is also understood that there are a number of values disclosed herein, and that each value is also herein disclosed as "about" that particular value in addition to the value itself. For example, if the value "10" is disclosed, then "about 10" is also disclosed. It is also understood that each unit falling within a range between two particular units are also disclosed. For example, if 10 and 15 are disclosed, then 11, 12, 13, and 14 are also disclosed.

As used herein, the terms "about" and "at or about" mean that the amount or value in question can be the designated value, approximately the designated value, or about the same as the designated value. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" mean that the subsequently described event, condition, component, or circumstance may or may not occur, and that the description includes instances where said event or circumstance occurs and instances where it does not.

As used herein, the term or phrase "effective," "effective amount," or "conditions effective to" refers to such amount or condition that is capable of performing the function or property for which an effective amount is expressed. As will be pointed out below, the exact amount or particular condition required may vary from one aspect or aspect to another, depending on recognized variables such as the materials employed and the processing conditions observed. Thus, it is not always possible to specify an exact "effective amount" or "condition effective to" for each aspect or aspect encompassed by the present disclosure. However, it should be understood that an appropriate effective amount or condition effective to achieve a desired results will be readily determined by one of ordinary skill in the art using only routine experimentation.

Disclosed are the components to be used to prepare disclosed compositions of the disclosure as well as the compositions themselves to be used within methods disclosed herein. These and other materials are disclosed herein, and it is understood that when combinations, subsets, interactions, groups, etc. of these materials are disclosed that while specific reference of each various individual and collective combinations and permutation cannot be explicitly disclosed, each is specifically contemplated and described herein. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight, of a particular component in a composition or article, denotes the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included. For example if a particular element or component in a composition or article is said to have 8% weight, it is understood that this percentage is relation to a total compositional percentage of 100%.

Each of the component starting materials disclosed herein are either commercially available and/or the methods for the production thereof are known to those of skill in the art.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A fiber-reinforced thermoplastic composition comprising:
   a) a polypropylene polymer component including a low flow grade polypropylene and a high flow grade polypropylene; where in the low flow grade polypropylene has a MFI of less than 20 g/10 min, and the high flow grade polypropylene has a MFI of greater than or equal to 20 g/10 min when measured at a temperature of 230° C. and under a 2.16 kg load; and
   b) a fiber reinforcement component,
   wherein the fiber-reinforced thermoplastic composition is capable of being vacuum formed.

2. The fiber-reinforced thermoplastic composition of claim 1, comprising:
   a) from 10 to 80 weight percent of the polypropylene polymer component; and
   b) from 20 to 90 weight percent of the fiber reinforcement component.

3. The fiber-reinforced thermoplastic composition of claim 1, wherein the fiber-reinforced thermoplastic composition has a melt flow rate (MFR) of between 14 and 18 g/10 minutes when measured at a temperature of 210 ° C. and under a 5 kg load.

4. The fiber-reinforced thermoplastic composition of claim 1, wherein the vacuum forming comprises a heater profile configured to heat a surface area at a perimeter of a plaque formed from the fiber-reinforced thermoplastic composition .

5. The fiber-reinforced thermoplastic composition of claim 4, wherein the heater profile is applied via a pressurized halogen heater.

6. The fiber-reinforced thermoplastic composition of claim 1, wherein the polypropylene polymer component comprises a polypropylene homo-polymer.

7. The fiber-reinforced thermoplastic composition of claim 1, wherein the polypropylene polymer component comprises a polypropylene co-polymer.

8. The fiber-reinforced thermoplastic composition of claim 1, wherein the fiber reinforcement component comprises a glass fiber.

9. The fiber-reinforced thermoplastic composition of claim 8, wherein the fiber reinforcement component comprises a long glass fiber having a length after extrusion or molding of from about 2 mm to about 15 mm.

10. The fiber-reinforced thermoplastic composition of claim 8, wherein the fiber reinforcement component comprises short glass fibers having a length after extrusion or molding of from about 0.1 mm to about 0.2 mm.

11. The fiber-reinforced thermoplastic composition of claim 1, further comprising one or more additives selected from the group consisting of a coupling agent, heat stabilizer, flow modifier, and colorant.

12. A fiber-reinforced thermoplastic composition comprising:
    a) a polypropylene polymer component including a low flow grade polypropylene and a high flow grade polypropylene; wherein the polypropylene polymer component comprises 30% high flow grade polypropylene and 70% low flow grade polypropylene relative to the polypropylene polymer component; and
    b) a fiber reinforcement component,
    wherein the fiber-reinforced thermoplastic composition is capable of being vacuum formed.

13. An article formed from the fiber-reinforced thermoplastic composition of claim 1.

14. The article of claim 13, wherein the article comprises an enclosure for an electrical component.

15. The article of claim 13, wherein the article is chemically resistant to a medical grade cleaner.

16. A thermoplastic composition comprising:
    a) a homopolymer component comprising polypropylene;
    a co-polymer component, wherein the co-polymer componenet has a MFI of less than 30 g/10 min, when measure at temperature of 230° C. and under 2.16 kg load;
    b) an impact modifier; and
    c) one or more of a flame retardant component and a fiber reinforcement component,
    wherein the thermoplastic composition is capable of being vacuum formed.

17. The thermoplastic composition of claim 16, further comprising one or more additives selected from the group consisting of a coupling agent, heat stabilizer, flow modifier, and colorant.

18. An article formed from the thermoplastic composition of claim 16.

19. The article of claim 18, wherein the article comprises an enclosure for an electrical component.

20. The article of claim 18, wherein the article is chemically resistant to a medical grade cleaner.

* * * * *